US007166694B2

(12) United States Patent
Zielinski et al.

(10) Patent No.: US 7,166,694 B2
(45) Date of Patent: Jan. 23, 2007

(54) VACCINE AGAINST CANCEROUS DISEASES WHICH IS BASED ON MIMOTOPES OF ANTIGENS EXPRESSED ON TUMOR CELLS

(76) Inventors: Christoph Zielinski, Dr. Heinrich Maierstrasse 20, Vienna (AT) A-1180; Otto Scheiner, Petersbachgasse 12b, Perchtoldsdorf (AT) A-2380; Erika Jensen-Jarolim, Arbeiterstrandbadstrasse 38, Vienna (AT) A-1210; Heimo Breiteneder, Kandlgasse 9/23, Vienna (AT) A-1070; Hubert Penamberger, Schwinglgasse 20, Vienna (AT) A-1230

( * ) Notice: Subject to any disclaimer, the term of this patent is extended or adjusted under 35 U.S.C. 154(b) by 494 days.

(21) Appl. No.: 10/257,603

(22) PCT Filed: Apr. 12, 2001

(86) PCT No.: PCT/EP01/04251

§ 371 (c)(1),
(2), (4) Date: Mar. 11, 2003

(87) PCT Pub. No.: WO01/78766

PCT Pub. Date: Oct. 25, 2001

(65) Prior Publication Data

US 2005/0100551 A1 May 12, 2005

(30) Foreign Application Priority Data

Apr. 13, 2000 (DE) .................. 100 18 403
Aug. 23, 2000 (DE) .................. 100 41 342

(51) Int. Cl.
C07K 7/04 (2006.01)
(52) U.S. Cl. ..................... 530/327; 424/185.1
(58) Field of Classification Search ............ None
See application file for complete search history.

(56) References Cited

U.S. PATENT DOCUMENTS

| 5,772,997 A | 6/1998 | Hudziak et al. |
| 5,801,005 A | 9/1998 | Cheever et al. |
| 5,869,445 A | 2/1999 | Cheever et al. |
| 6,610,297 B1 * | 8/2003 | Kricek et al. ............ 424/178.1 |

FOREIGN PATENT DOCUMENTS

| JP | 117165 | 5/1993 |
| WO | WO 96/18409 A1 | 6/1996 |
| WO | WO 99/33969 | 8/1999 |
| WO | WO 99/57981 A1 | 11/1999 |
| WO | WO 01/08636 A2 | 2/2001 |

OTHER PUBLICATIONS

Zhu et al. PMSA mimotype isolated from phage displayed peptide library can induce PMSA specific immune response. Cell Research 9:271-280 (1999).*
Perosa et al. Ann. N.Y. Acad. Sci. 1051: 672-683, 2005.*
DeGruijl et al. Nature Medicine 5(10): 1124-1125, Oct. 1999.*
Mellman I. The Scientist 20(1): 47, 2006.*
Bodey B. et al. Anticancer Research 20: 2665-2676, 2000.*
Baselga et al. (1988) "Recombinant Humanized Anti-HER2 Antibody (Herceptin) Enhances the Antitumor Activity of Paclitaxel and Doxorubicin against HER2/neu Overexpressing Human Breast Cancer Xenografts", *Cancer Research* 58: 2825-2831.
Baselga. et al. (2000) "Phase I Studies of Anti-Epidermal Growth Factor Receptor Chimeric Antibody C225 Alone and in Combination With Cisplatin", *Journal of Clinical Oncology*, vol. 18, No. 4, pp. 904-914.
Behr et al. (1999) Low-*versus* High-Dose Radioimmunotherapy with Humanized Anti-CD22 or Chimeric Anti-CD20 Antibodies in a Broad Spectrum of B Cell-associated Malignancies, *Clinical Cancer Research* vol. 5. 3304s-3314s.
Braun et al. (1999) Monoclonal Antibody Therapy with Edrecolomab in Breast Cancer Patients: Monitoring of Elimination of Disseminated Cytokeratin-positive Tumor Cells in Bone Marrow *Clinical Cancer Research* vol. 5, 3999-4004.
Cha et al. (1996) "Random phage mimotopes recognized by monoclonal antibodies against the pyruvate dehydrogenase complex-E2 (PDC-E2)", *Proc. Natl. Acad. Sci. USA*, vol. 93, pp. 10949-10954 Immunology.
D'Mello et al. (1997) "Definition of the Primary Structure of Hepatitis B Virus (HBV) pre-S Hepatocyte Binding Domain Using Random Peptide Libraries" *Virology* vol. 237, pp. 319-326.
Huang et al. (1999) "Epidermal Growth Factor Receptor Blockade with C225 Modulates Proliferation, Apoptosis, and Radiosensitivity in Squamous Cell Carcinomas of the Head and Neck" *Cancer Research* vol. 59, pp. 1935-1940.
Martin. et al. (1999) "Expression of the 17-1A antigen in gastric and gastro-oesophageal junction adenocarcinomas: a potential immunotherapeutic target?" *J. Clin. Pathol*, vol. 52, pp. 701-704.
McCormick et al. (1999) "Rapid production of specific vaccines for lymphoma by expression of the tumor-derived single-chain Fv Epitopes in tobacco plants" *Proc. Natl. Acad. Sci USA* vol. 96, pp. 703-708 Medical Sciences.
Milpied. et al. (2000) "Humanized anti-CD20 monoclonal antibody (Rituximab) in post transplant B-lymphoproliferative disorder: A retrospective analysis on 32 patients" Annals of Oncology II Suppl. S113-S116 Kluwer Academic Publishers.

(Continued)

*Primary Examiner*—Larry R. Helms
*Assistant Examiner*—David Humphrey
(74) *Attorney, Agent, or Firm*—Milbank, Tweed, Hadley & McCloy LLP (57) ABSTRACT

The present invention provides a method for producing a vaccine against cancerous disease, and the vaccine itself. This method involves first using one or more antibodies that are specifically effective against one or more antigens specially expressed by the tumor cells to select one or more mimotopes of said antigens from a phage peptide library. To obtain the vaccine, said mimotopes are conjugated to a macromolecular carrier singly or multiply in the form of their mono-, di-, tri- or oligomers. When administered, the inventively produced vaccine leads to a humoral immune response and thus to the formation of an active immunity as a consequence of vaccination.

24 Claims, 2 Drawing Sheets

OTHER PUBLICATIONS

Orlandi et al. (1994) "Antigenic and Immunogenic mimicry of the HER2/neu oncoprotein by phage-displayed peptides" *Eur. J. Immunol.* vol. 24, pp. 2868-2873.

Poczatek et al (1999) "Ep-Cam Levels in Prostatic Adenocarcinoma and Prostatic Intraepithelial Neoplasia" *The Journal of Urology*, vol. 162, pp. 1462-1466.

Punt (1998) "New Drugs in the Treatment of Colorectal Carcinoma" *CANCER*, vol. 83, No. 4 pp. 679-689.

Riethmuller et al. (1994) "Randomised trial of monoclonal antibody for adjuvant therapy of resected Dukes' C colorectal carcinoma" *The Lancet*, vol. 343, pp. 1177-1183.

Samonigg et al. (1999) "A Double-Blind Randomized-Phase II Trial Comparing Immunization with Antiidiotype Goat Antibody Vaccine SVC 106 Versus Upspecific Goat Antibodies in Patients with Metastatic Colorectal Cancer" *Journal of Immunotherapy*, vol. 22(6): pp. 481-488.

Stoute et al. (1995) "Induction of Humoral Immune Response against *Plasmodium falciparum* Sporozoites by Immunication with a Synthetic Peptide Mimotope Whose Sequence Was Derived from Screening a Filamentous Phage Epitope Library" *Infection and Immunity*, vol. 63, No. 3 pp. 934-939.

Treon et al. (2000) "Treatment of multiple myeloma by antibody mediated immunotherapy and induction of myeloma selective antigens" *Annals of Oncology* II Supp S107-S111.

Turpen et al. (1995) "Malarial Epitopes Expressed on the Surface of Recombinant Tobacco Mosaic Virus" *BiolTechnology* vol. 13, pp. 53-57.

Zwick, et al. (1998) "Phage-displayed peptide libraries" *Current Opinion in Biotechnology*, vol. 9 pp. 427-436.

Mittelman, Abraham et al., "Human high molecular weight melanoma-associated antigen (HMV-MAA) mimicry by mouse anti-idiotype monoclonal antibody MK2-23: Induction of humoral anti-HMV-MAA Immunity and prolongation of survival in patients with stage IV melanoma," Proc. Natl. Acad. Sci. USA, vol. 89, pp. 446-470. Jan. 1992.

Mittelman, A. et al., "Active Specific Immunotherapy in Patients with Melanoma. A Clinical Trial with Mouse Antiidiotypic Monoclonal Antibodies Elicited with Syngeneic Anti-High-Molecular-Weight-Melanoma-Associated Antigen Monoclonal Antibodies," J. Clin. Invest. Dec. 1990, 86, 2136-2144.

Geiser, Martin et al., "Identification of the Human Melanoma-associated Chondroitin Sulfate Proteoglycan Antigen Epitope Recognized by the Antitumor Monoclonal Antibody 763.74 from a Peptide Phage Library," Cancer Research 59, 905-910, Feb. 15, 1999.

Mittelman, Abraham et al., "Human High Molecular Weight-Melanoma Associated Antigen Mimicry by Mouse Anti-Idiotypic Monoclonal Antibody MK2-23: Modulation of the Immunogenicity in Patients with Malignant Melanoma," Clinical Cancer Research vol. 1, 705-173, Jul. 1995.

Ziai, M. Reza et al., "Analysis with Monoclonal Antibodies of the Molecular and Cellular Heterogeneity of Human High Molecular Weight Melanoma Associated Antigen," Cancer Research 47, 2474-2480, May 1, 1987.

Price, Michael et al., "Enhancement of Cell-mediated Immunity in Melanoma Patients Immunized with Murine Anti-Idiotypic Monoclonal Antibodies (MELIMMUNE) That Mimic the High Molecular Weight Proteoglycan Antigen," Clinical Cancer Research vol. 4, 2363-2370 Oct. 1998.

Ferrone, S. et al., "Active Specific Immunotherapy of Malignant Melanoma and Peptide Mimics of the Human High-Molecular-Weight Melanoma-Associated Antigen," Recent Results Cancer Res., 2001, 158, 231-5).

Wison, Barry S. et al., Distribution and Molecular Characterization of a Cell-Surface and a Cytoplasmic Antigen Detectable in Human Melanoma Cells with Monoclonal Antibodies, Int. J. Cancer: 28, 293-300 (1981).

Leitner, Agnes et al., "A mimotope defines by phage display inhibits IgE binding to the plant panallergen profilin," Eur. J. Immunol. 1998, 28:2921-2927.

* cited by examiner

SEQUENCE LISTING

<160> NUMBER OF SEQ ID NOS: 11

<210> SEQ ID NO 1
<211> LENGTH: 20
<212> TYPE: PRT
<213> ORGANISM: homo sapiens

<400> SEQUENCE: 1

Ala Glu Gly Glu Phe Ala Thr Leu Met Gln Ile Ile Ser Gln Gly Gly
1               5                   10                  15

Gly Gly Gly Cys
            20

<210> SEQ ID NO 2
<211> LENGTH: 5
<212> TYPE: PRT
<213> ORGANISM: homo sapiens

<400> SEQUENCE: 2

Gly Gly Gly Gly Gly
1               5

<210> SEQ ID NO 3
<211> LENGTH: 9
<212> TYPE: PRT
<213> ORGANISM: homo sapiens

<400> SEQUENCE: 3

Ala Thr Leu Met Gln Ile Ile Ser Gln
1               5

<210> SEQ ID NO 4
<211> LENGTH: 5
<212> TYPE: PRT
<213> ORGANISM: homo sapiens

<400> SEQUENCE: 4

Ala Glu Gly Glu Phe
1               5

<210> SEQ ID NO 5
<211> LENGTH: 6
<212> TYPE: PRT
<213> ORGANISM: homo sapiens

<400> SEQUENCE: 5

Gly Gly Gly Gly Gly Cys
1               5

<210> SEQ ID NO 6
<211> LENGTH: 11
<212> TYPE: PRT
<213> ORGANISM: homo sapiens

<400> SEQUENCE: 6

Cys Trp Ala Glu Met Leu Leu Pro Leu Ala Cys
1               5                   10

<210> SEQ ID NO 7
<211> LENGTH: 9
<212> TYPE: PRT
<213> ORGANISM: homo sapiens

```
-continued

<400> SEQUENCE: 7

Arg Ser Arg Leu Trp Ala Val Met Glu
1               5

<210> SEQ ID NO 8
<211> LENGTH: 11
<212> TYPE: PRT
<213> ORGANISM: homo sapiens

<400> SEQUENCE: 8

Cys Leu Ala Asp Pro Phe Ile Pro His Gly Cys
1               5                   10

<210> SEQ ID NO 9
<211> LENGTH: 11
<212> TYPE: PRT
<213> ORGANISM: homo sapiens

<400> SEQUENCE: 9

Cys His Pro Thr Leu Leu Trp Pro Asp Phe Cys
1               5                   10

<210> SEQ ID NO 10
<211> LENGTH: 11
<212> TYPE: PRT
<213> ORGANISM: homo sapiens

<400> SEQUENCE: 10

Cys Tyr Pro Ser Leu Leu Leu His Leu Pro Cys
1               5                   10

<210> SEQ ID NO 11
<211> LENGTH: 11
<212> TYPE: PRT
<213> ORGANISM: homo sapiens

<400> SEQUENCE: 11

Cys Tyr Val Leu Pro Ser Gly Leu Gln Ser Cys
1               5                   10
```

VACCINE AGAINST CANCEROUS DISEASES WHICH IS BASED ON MIMOTOPES OF ANTIGENS EXPRESSED ON TUMOR CELLS

This application claims benefit of priority to German Patent Application No. DE 100 41 342.0, filed Apr. 13, 2000 and German Patent Application No. DE 100 18 403.3, filed Aug. 23. 2000.

FIELD OF INVENTION

The present invention relates to a method for producing a vaccine against cancerous diseases and to said vaccine itself.

BACKGROUND OF INVENTION

In recent years there has been a steady increase in cancerous diseases in Western industrial nations. For example, roughly 23,000 men and 29,000 women a year develop colonic and rectal cancer in Germany, the risk of disease rising gradually with age. Malignant lymphomas constitute about 5 percent of all cancer cases, about 9,000 persons a year developing non-Hodgkin's lymphoma in Germany—with an upward trend. Breast cancer even affects about 10 percent of all women in Western industrial nations.

Methods hitherto known for treating cancerous diseases aim above all at early recognition of the illness and at surgical methods or selective destruction of tumor cells. These methods have the disadvantages that they do not permit effective prophylaxis against the genesis of the cancerous disease and that treatment for example by chemotherapy involves very considerable side effects for the patient.

Accordingly, it is the problem of the present invention to provide a vaccine against cancerous diseases that makes it possible to effectively prevent cancerous diseases and thus clearly reduce the risk of such diseases.

SUMMARY OF INVENTION

The invention is based on the finding that such a vaccine can be obtained by a method utilizing antibodies that are effective against an antigen formed by the tumor cells in order to obtain mimotopes of said antigen that can be used to stimulate an endogenous immune response.

The subject matter of the present invention is a method for producing a vaccine against cancerous diseases that is characterized by first using one or more endogenous or synthetic antibodies that are specifically effective against one or more antigens specially expressed by the tumor cells to select one or more mimotopes of said antigens from a phage peptide library and then conjugating said mimotopes to a macromolecular carrier.

The subject matter of the present invention is further a vaccine against cancerous diseases to be produced by said method.

The inventive method obtains vaccines against cancerous diseases even if the nature or structure of the corresponding antigen is unknown or not known in detail.

In addition, the obtained vaccines are phage-free and therefore also very well suited for vaccination in the human system. Thus, the vaccine in particular also permits a prophylaxis against cancerous diseases, i.e., the inventive vaccine is capable of protecting against a potential cancerous disease by active immunization so that it does not arise in the first place. However, the vaccine can also be used to treat an already existing cancerous disease.

In a preferred embodiment, the inventive method uses antibodies that have as such already proved effective against cancerous diseases in clinical tests. Thus, administration of the vaccine induces the formation of endogenous antibodies against those antigens of the cancer cells against which the clinically tested antibodies are effective. This increases the effectiveness of the vaccine.

Conjugation of the mimotopes obtained in the inventive method to the macromolecular carrier can be effected in any desired way, for example, by genetic engineering or chemically, whereby the mimotopes are bound to the carrier by a chemical reaction.

The mimotopes are preferably provided before conjugation to the carrier with a linker, for example, a short-chain oligopeptide. Conjugation to the carrier is then effected via the linker.

In a preferred embodiment, the mimotopes are conjugated to the carrier by genetic engineering, i.e., the vaccine is produced by inserting a DNA or RNA sequence coding for the vaccine into an expression system so that the total vaccine, i.e., the carrier with the mimotopes bound thereto, is expressed.

The mimotopes found with the aid of the antibodies can be conjugated to a macromolecular carrier as mono-, di-, tri- or oligomers. Such conjugations are described, for example, in the publication by Th. H. Turpen, S. J. Reinl, Y. Charoenvit, S. L. Hoffman, V. Fallarme in Bio/Technology 1995, vol. 13, pp. 53 to 57, by the example of conjugating epitopes to macromolecular carriers. The described procedures can be transferred analogously to the conjugation of mimotopes to the macromolecular carrier used in the inventive method. The disclosure of this publication is incorporated herein by reference.

In the stated publication the epitopes are conjugated by genetic engineering. The RNA portions coding for the epitopes are thereby integrated into the RNA sequence of the carrier either singly or one or more times lined up one after the other. This obtains the expression of mono-, di- or oligomeric epitope conjugates. According to the present invention, the RNA or DNA portions coding for the mimotopes are integrated into the RNA or DNA sequence of the carrier as mono-, di-, tri- or oligomeric mimotope sequences.

To further increase the immunogenicity, the mono-, di-, tri- or oligomeric mimotopes can be bound to the macromolecular carrier both singly and in multiple form.

In a preferred embodiment, the present invention provides a method for producing a vaccine against adenocarcinomas of the gastrointestinal tract, carcinoma of the prostate, breast cancer (mastocarcinoma), multiple myeloma, B-lymphoproliferative post-transplant syndrome, B-cell malignoma and chronic lymphatic leukemia. The vaccine produced by the method can counteract the genesis of said kinds of cancer.

The antibodies used for the inventive production of the vaccine against cancerous diseases are specifically effective against antigens specially expressed by tumor cells. Said antibodies may firstly be endogenous ones, as are present, for example, in the blood-serum of affected patients as a result of the humoral immune response to the antigen or antigens. The production or isolation of said antibodies is effected by known, conventional methods.

Secondly, one can also use synthetic antibodies or antibody preparations that have optionally been humanized.

Further, the inventive method can use monoclonal antibodies, as well as polyclonal antibodies.

In one embodiment, the endogenous or synthetic antibodies used in the inventive method include those antibodies that trigger an antibody dependent cellular cytotoxicity (ADCC reaction) or recognize a receptor for a growth factor of the tumor cells acting as an antigen. The use of such antibodies ensures an especially pronounced effect of the vaccine obtained by the inventive method.

The endogenous or synthetic antibodies used in this embodiment preferably include those antibodies that are specifically effective against the HER-2/neu protein expressed by the tumor cells or the epithelial glycoprotein antigen, C017-1A, or the phosphoprotein surface antigen on lymphocytes, CD20, or the epidermal growth factor (EGF) receptor. The use of such antibodies above all guarantees very good effectiveness of the vaccine produced by the inventive method against breast cancer (mastocarcinoma), adenocarcinomas of the gastrointestinal tract, carcinoma of the prostate, multiple myeloma, B-lymphoproliferative post-transplant syndrome, B-cell malignoma and head-neck tumors.

The HER-2/neu protein is a receptor for a growth factor under whose control the tumor cells grow. Antibodies against the HER-2/neu protein are described, for example, in U.S. Pat. No. 5,772,997. The disclosure of this patent print is incorporated herein by reference.

Of the antibodies effective against the HER-2/neu protein, the inventive method preferably uses the clinically tested antibody preparation, herceptin, from Genentech Inc. This antibody preparation, when added to conventional chemotherapy in breast cancer patients, has already brought about a clear improvement of the response rate to the patients' treatment. Herceptin is a humanized monoclonal antibody obtained from mice. Herceptin is effective against the antigen HER-2/neu, which is frequently overexpressed as a growth factor receptor on tumor cells. Specially in breast cancer tumors, the HER-2/neu antigen is expressed specifically on the cell surface in roughly 20 to 30 percent of cases. The administration of herceptin leads to commencement of natural death of the tumor cells expressing HER-2/neu. The inventively produced vaccine is effective particularly against the kinds of cancer in which there is an expression of HER-2/neu on the tumor cells, e.g., against breast cancer.

In a further embodiment, the endogenous or synthetic antibodies used in the inventive method include the clinically tested antibody preparation, Panorex, from GlaxoWellcome. This antibody preparation is also called Edrecolamab. Panorex is a monoclonal antibody obtained from mice. As reported by Riethmüller et al., Lancet 343 (1994) 1177–83, Panorex is directed against the epithelial glycoprotein antigen C017-1A. The disclosure of this publication is incorporated herein by reference. Panorex is effective in particular against adenocarcinomas of the gastrointestinal tract (Punt, Cancer 83 (1998) 679–89; Martin et al., J. Clin. Pathol. 52 (1999) 701–4; Samonigg et al., J. Immunother. 22 (1999) 481), carcinoma of the prostate (Poczatek et al., The Journal of Urology 162 (1999) 1462–6) and against breast cancer (Braun et al., Clin. Cancer Res. 5 (1999) 3999–4004). The disclosure of these publications is incorporated herein by reference. Therefore, the inventively produced vaccine is effective particularly against these kinds of cancer.

In a further embodiment, the endogenous or synthetic antibodies used in the inventive method include the clinically tested antibody preparation, MabThera, from Genentech Inc. This antibody preparation is also called Rituxan (IDEC Pharmaceuticals) or Rituximab (Hoffmann-LaRoche). MabThera is a humanized, monoclonal antibody obtained from mice and directed against the phosphoprotein surface antigen on lymphocytes, CD20. MabThera is effective in particular against multiple myeloma (Treon et al., Ann. Oncol. 11 (2000) 107–11), against B-lymphoproliferative post-transplant syndrome (Milpied et al, Ann. Oncol. 11 (2000) 113–116), against B-cell malignoma (Behr et al., Clin. Cancer Res. 5 (1999) 3304–3314) and against lymphatic leukemia. The disclosure of these publications is incorporated herein by reference. Therefore, the inventively produced vaccine is effective particularly against these kinds of cancer.

In a further embodiment, the endogenous or synthetic antibodies used in the inventive method include the antibody preparation, IMC-C225 (Cetuximab), from ImClone, which is undergoing clinical testing. IMC-C225 (Cetuximab) is a chimerized monoclonal antibody directed against the epidermal growth factor (EGF) receptor. IMC-C225 (Cetuximab) is effective in particular against head-neck tumors (Hueng et al., Cancer Res. 59 (1999), 1935–40; Baselga et al., J. Clin. Oncol. 18 (2000) 904–14). The disclosure of these publications is incorporated herein by reference. The vaccine produced by the inventive method is effective particularly against these kinds of cancer.

The mimotopes selected from the phage peptide libraries or the mimotope conjugates are preferably prepared using a vegetal expression system, such as the tobacco mosaic virus system. In this system, the expression of the mimotopes or mimotope conjugates can be effected by transient infection of the host plants with tobacco mosaic viruses. The thus expressed mimotopes and mimotope conjugates are endotoxin- and phage-free and, thus, particularly suitable for use in the inventive method for producing a vaccine or as the vaccine itself. This expression system is also particularly suitable for producing the mimotopes or mimotope conjugates in a large quantity.

In the following, the inventive method will be described in detail.

The endogenous or synthetic antibodies are used in the inventive method to select from phage peptide libraries suitable peptide mimotopes of the antigens against which antibodies are specifically effective. A survey of phage peptide libraries and associated literature is given by M. B. Zwick, J. Shen and J. K. Scott in Current Opinion in Biotechnology 1998: 427–436. The disclosure of this publication is incorporated herein by reference.

Phage peptide libraries consist of filamentous phages that express different peptides on their surface in a very great variation range. Conventional selection methods are used to find the matching peptide mimotopes from these libraries using the antibodies effective against the special antigen. It is to be noted that the found mimotopes do not have to match the corresponding epitope of the antigen in their chemical nature.

The thus selected mimotopes are characterized by DNA sequencing. According to the pattern of the found sequences, mimotopes are produced as fision protein with macromolecular carrier or synthesized and conjugated chemically to the macromolecular carrier. Said conjugation can be effected for example by connecting an albumen-binding protein (ABP), as is expressed for example by streptococci, with the mimotope protein. The connection of ABP and proteins is described by S. Baumann, P. Grob, F. Stuart, D. Pertlik, M. Ackermann and M. Suter in Journal of Immunological Methods 221 (1998) 95–106. The disclosure of this publication is incorporated herein by reference.

The step of conjugating the mimotopes to macromolecular carrier guarantees that administration of the vaccine induces an immune response of the body, i.e., this step is taken in order to make the mimotopes immunogenic.

The expression of the found mimotope proteins or mimotope conjugate proteins can be effected by systemic transient infection of vegetal expression systems (host plants) such as *Nicotiana tabacum* or *Nicotiana benthamiana* by the genomic and infective RNA from recombinant tobacco mosaic viruses (TMV) or by complete recombinant TMV particles.

For this purpose, the DNA sequence coding for the foreign protein is first spliced into a cDNA copy of the TMV located in a plasmid so that this sequence comes under the control of the subgenomic promoter for the original coat protein of the TMV. In the case of the mimotope conjugate, fusion to the ABP is first effected. For this purpose, the cDNA coding for the mimotope is joined to the 3' end of the cDNA coding for the ABP in the same reading frame. The resulting cDNA of the fusion protein ABP mimotope is inserted into a cDNA copy of the TMV genome. Thus this sequence comes under the control of the subgenomic promoter for the original coat protein of the TMV. An RNA transcript of the recombinant TMV genome is then synthesized in vitro. This RNA is infective and is applied to wounded leaves of the abovementioned host plants. Synthesis of the viral proteins and the desired foreign protein occurs in the cytoplasm of the host cells.

This expression method permits the mimotope proteins to be obtained easily in endotoxin-free form even on a large scale.

However, the expression or production of the found mimotype proteins can also be effected by conventional methods, for example expression in *E. coli* bacteria.

In this case, for conjugating ABP and mimotope protein a single-strand DNA sequence of the selected mimotopes is first obtained and double-strand DNA produced therefrom. This DNA is spliced into the expression vector pSB511. The resulting construct from information for mimotope and ABP is used for transforming competent *E. coli* XL-1 cells. After amplification and harvest of the cells, the recombinant protein can be purified by NiNTA agarose.

BRIEF DESCRIPTION OF DRAWINGS

In the following the present invention will be illustrated further with reference to an example and the enclosed figures, which show:

FIG. 1 depicts the results of immunization with the conjugate SEQ ID NO: 1-KLH using IgG1.

FIG. 2 depicts the results of immunization with the conjugate SEQ ID NO: 1 using IgG2a.

FIG. 3 depicts the results of immunization with the conjugate SEQ ID NO: 1-TT using IgG1.

FIG. 4 the results of immunization with the conjugate SEQ ID NO: 1-TT using IgG2a.

DETAILED DESCRIPTION OF INVENTION

Example 1

Identification of Herceptin Mimotopes

The wells of a Maxisorb plate from Nunc were coated with a monoclonal mouse antibody directed against the constant Fc region of human IgG, in a concentration of 10 μg/ml PBS for the duration of 16 hours.

After washing the wells and saturating free binding sites by BSA, the herceptin antibody was bound to the monoclonal mouse antibody by its Fc region. Herceptin was incubated in a concentration of 10 μg/ml PBS for two hours.

After further routine washing steps, the wells of the Maxisorb plate were covered with the phage library. This library contained filamentous M13 phages in whose pVIII gene coding for a phage coat protein, nucleotide sequences coding for peptides with a length of 9 amino-acid residues were inserted. This library contained $10^9$ individual phage clones differing in the sequence of their inserts.

Phages that bound to the herceptin by these peptides were detached from the herceptin by pH lowering. Suitable *E. coli* host cells were infected with the thus eluted phages and amplified by growth of the bacterial cells. This process from the binding to the antibody up to the amplification of specifically bound phages is called a panning round. Three panning rounds were performed, and DNA isolated from the resulting phage clones and sequenced. The most frequently identified sequence coding for an inserted peptide was used as a basis for synthesis of the vaccine matter conjugates.

The peptide fused to the pVIII on the phage surface is not quite terminal but has at its N-terminus 5 amino-acid residues of the pVIII protein. These were included in the solid phase synthesis of the peptide. Further, the peptide was provided at the C-terminus with a linker of the GlyGlyGlyGlyGly (SEQ ID NO: 2) type to permit formation of the native 3D structure on the conjugant as well. A C-terminal Cys was likewise joined to permit the coupling reaction by organic-chemical means to the carrier proteins.

Example 2

Immunization Scheme

A) Immunization of Mice.

One of the mimotopes with the amino acid sequence ATLMQIISQ (SEQ ID NO: 3) found in the way described under 1 was used for immunization. At the N-terminus of this sequence there were 5 amino-acid residues of the pVIII protein, i.e., the residues AEGEF (SEQ ID NO: 4), as stated under 1.

Before coupling, the mimotope was provided at its C-terminus with the linker GGGGGC (SEQ ID NO: 5). The amino acid sequence coupled to the coupling partner was accordingly AEGEFATLMQIISQGGGGGC (SEQ ID NO: 1).

Two coupling partners (=carrier proteins) with SEQ ID NO: 1 were tested, namely KLH and tetanus toxoid. Two immunization routes were used. Subcutaneously, 15 μg of the particular conjugate was used, intraperitoneally 150 μg in each case. The adjuvant used was Gerbu adjuvant. Each subcutaneously immunized group had 5 mice, each i.p. immunized group 3 mice. The control groups (each with 3 mice) were only administered the conjugant with Gerbu adjuvant.

After the first immunization (=priming), boostering was done twice at a 2-week interval. Two weeks after the 2nd boostering a titer control of the antibodies directed against the mimotope was performed. The detection of specific antibodies was effected by ELISAs.

96-well plates were coated with the corresponding conjugates (=TT plus SEQ ID NO: 1 or KLH plus SEQ ID NO: 1). As a control for non-specific antibody bonds to the conjugant alone, the wells were coated with TT or KLH.

Serums of the mouse groups immunized with tetanus toxoid plus SEQ ID NO: 1 were tested for KLH plus SEQ ID NO: 1 alone. Serums of the mouse groups immunized with KLH plus SEQ ID NO: 1 were tested for TT plus SEQ ID NO: 1 and TT alone. For isotype determination of the mimotope-specific antibodies, corresponding rat anti-mouse IgG1 and anti-mouse IgG2a were used.

For detecting the bond, a horseradish peroxidase (HRP) of conjugated anti-rat IgG antibodies followed. HRP enters into a color reaction with a substrate. The result of this color reaction can be quantified by photometer. The absorption coefficient (OD) is measured.

The results of the immunizations are shown in Tables 1 to 4 and FIGS. 1 to 4.

The titer control was performed after the 3rd immunization, as mentioned above. The serums were pooled. The dilution was 1:2500.

Figure 1:
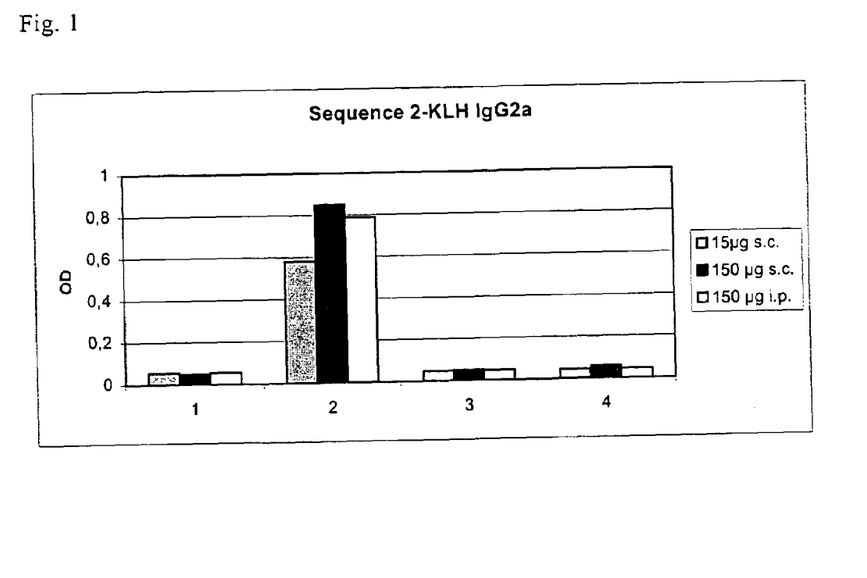
Figure 2:
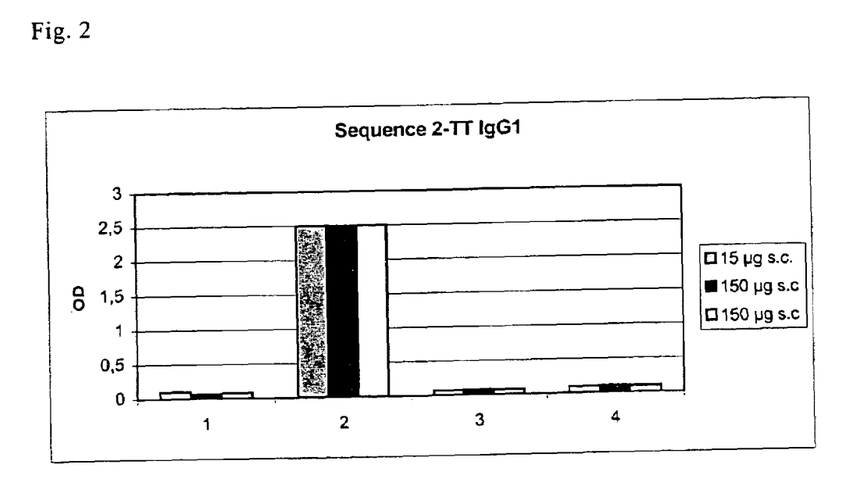

FIGS. 1 and 2 show the results of immunizations with SEQ ID NO: 1 coupled to KLH stated in Tables 1 and 2. Bar groups 1 to 4 correspond as follows:
(1) Preimmune serums on mimotope plus carrier protein,
(2) Postimmune (after 2nd boostering) serums on mimotope plus carrier protein,
(3) Preimmune serums on carrier protein without mimotope,
(4) Postimmune serums on carrier protein without mimotope.

Figure 3:
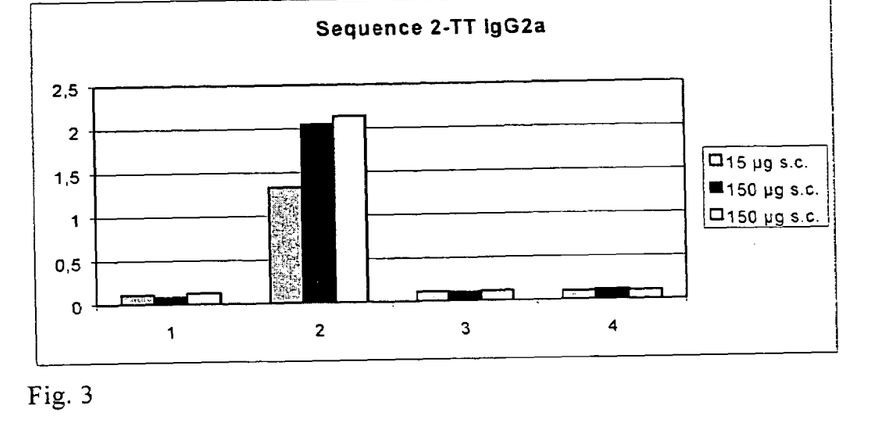
Figure 4:
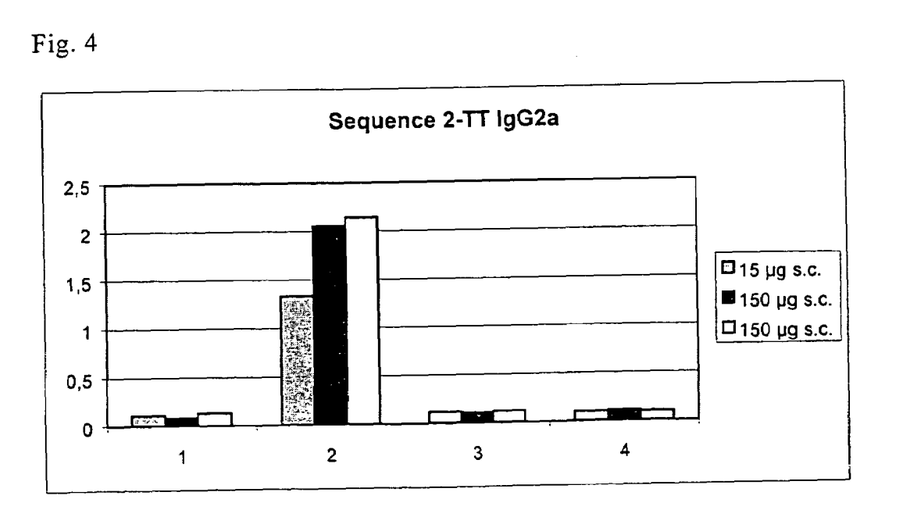

FIGS. 3 and 4 show the results of immunizations with SEQ ID NO: 1 coupled to TT. The meaning of the bars is as for FIGS. 1 and 2.

The immunization data clearly show that subcutaneous or i.p. administration of mimotope conjugated to KLH or TT induced a mimotope-specific antibody response. This antibody response could be observed both with IgG1 and with IgG2a (2nd group of bars in FIGS. 1 to 4).

TABLE 1

Immunization with SEQ ID NO: 1-KLH, coating with SEQ ID NO: 1-TT, control coating with TT.

| IgG1 | SEQ ID NO: 1-TT | | Non-specific binding to TT | |
|---|---|---|---|---|
| | Preimmune | Postimmune | Preimmune | Postimmune |
| SEQ ID NO: 1-KLH 15 µg s.c. | 0.079 | 2.5 | 0.071 | 0.065 |
| SEQ ID NO: 1-KLH 150 µg s.c. | 0.417 | 2.5 | 0.048 | 0.085 |
| SEQ ID NO: 1-KLH 150 µg i.p. | 0.137 | 2.5 | 0.069 | 0.063 |

TABLE 2

Immunization with SEQ ID NO: 1-KLH, coating with SEQ ID NO: 1-TT, control coating with TT.

| IgG2a | SEQ ID NO: 1-TT | | Non-specific binding to TT | |
|---|---|---|---|---|
| | Preimmune | Postimmune | Preimmune | Postimmune |
| SEQ ID NO: 1-KLH 15 µg s.c. | 0.079 | 0.581 | 0.047 | 0.045 |
| SEQ ID NO: 1-KLH 150 µg s.c. | 0.049 | 0.849 | 0.05 | 0.059 |
| SEQ ID NO: 1-KLH 150 µg i.p. | 0.055 | 0.787 | 0.047 | 0.045 |

TABLE 3

Immunization with SEQ ID NO: 1-TT, coating with SEQ ID NO: 1-KLH, control coating with KLH.

| IgG1 | SEQ ID NO: 1-KLH | | Non-specific binding to KLH | |
|---|---|---|---|---|
| | Preimmune | Postimmune | Preimmune | Postimmune |
| SEQ ID NO: 1-TT 15 µg s.c. | 0.102 | 2.5 | 0.074 | 0.094 |
| SEQ ID NO: 1-TT 150 µg s.c. | 0.07 | 2.5 | 0.078 | 0.102 |
| SEQ ID NO: 1-TT 150 µg s.c. | 0.079 | 2.5 | 0.074 | 0.094 |

TABLE 4

Immunization with SEQ ID NO: 1-TT, coating with sequence SEQ ID NO: 1-KLH, control coating with KLH.

| IgG2a | SEQ ID NO: 1-KLH | | Non-specific binding to KLH | |
|---|---|---|---|---|
| | Preimmune | Postimmune | Preimmune | Postimmune |
| SEQ ID NO: 1-TT 15 15 µg s.c. | 0.111 | 1.329 | 0.116 | 0.1 |
| SEQ ID NO: 1-TT 150 µg s.c. | 0.083 | 2.054 | 0.102 | 0.111 |
| SEQ ID NO: 1-TT 150 µg s.c. | 0.129 | 2.143 | 0.116 | 0.1 |

B) Immunizations of Rabbits.

Mimotope peptides CWAEMLLPLAC (SEQ ID NO: 6); RSRLWAVME (SEQ ID NO: 7); CLADPFIPHGC (SEQ ID NO: 8) and ATLMQIISQ (SEQ ID NO: 3) were synthesized, coupled to KLH chemically by succinimide-thiopyridine linker and purified by gel filtration. For immunizing rabbits, 200 µg conjugate or $10^{10}$ phage particles (with the mimotope ATLMQIISQ) per dose was used. The immunizations were effected subcutaneously once with complete Freund's adjuvant, followed by five further doses of the antigen in incomplete Freund's adjuvant at 14-day intervals. Blood samples were taken before (preimmune serum) and one week after the last dose.

The rabbit serums were tested for IgG induction against the immunogen (mimotope peptide) as well as the carrier KLH alone by the ELISA assay. As already shown with mice, IgG directed specifically against mimotopes could also be achieved in rabbits. This is shown by the following example:

TABLE 5

Immunization of rabbits with KLH-mimotope peptides.

| | Rabbits immunized with KLH mimotope: | | | | |
|---|---|---|---|---|---|
| IgG against KLH mimotope* | SEQ ID NO: 6 | SEQ ID NO: 7 | SEQ ID NO: 8 | SEQ ID NO: 3 | SEQ ID NO. 3 (Phage) |
| SEQ ID NO: 6 | 0.43 | 0.39 | 0.37 | 0.32 | 0.35 |
| SEQ ID NO: 7 | 0.39 | 0.34 | 0.22 | 0.35 | 0.85 |
| SEQ ID NO: 8 | 0.38 | 0.41 | 0.35 | 0.34 | 0.28 |
| SEQ ID NO: 3 | 0.55 | 0.42 | 0.42 | 0.33 | 0.45 |
| KLH | 0.29 | 0.31 | 0.16 | 0.29 | 0.03 |

*Binding to KLH mimotopes (Relative OD in ELISA)

Example 3

Detection of Specificity

A) Inhibition of Herceptin by Phage Mimotopes in ELISA.

For detecting the inhibition of the binding of herceptin and HER-2/neu by mimotopes, one proceeds as follows:

Her-2/neu is recognized in the cytomembranes of the cell line SKBR3 in ELISA by the humanized monoclonal antibody herceptin. For the ELISA inhibition assay one tries to prevent this bond by preincubation with mimotopes on phages or KLH as carrier.

The wells of a 96-well ELISA plate (Nunc) were coated with membrane fractions of the Her-2/neu overexpressing cell line SKBR3 and as a control for non-specific antibody bonds with membrane fractions of the Her-2/neu negative cell line HTB 132 in PBS overnight.

Herceptin (anti-Her-2/neu antibody) was treated likewise overnight by preincubation with different antigens: mimotopes, control mimotopes or buffers.

The next day, non-specific binding sites were blocked by 3 percent BSA in PBS. Herceptin as well as herceptin after preincubation with relevant and irrelevant phage mimotopes or by mimotopes on KLH as well as on KLH alone were applied to the coated, blocked ELISA plate in a repeated test. Bound herceptin could be detected with a horseradish peroxidase (HRP) coupled monoclonal anti-human IgG. HRP enters into a color reaction with the substrate. The result of this color reaction can be quantified by photometer. The absorption coefficient of 450/630 nm (OD) is determined.

The result was an inhibition of reactivity with the Her-2/neu of the SKBR3 membranes as a diminution of the signal when herceptin had been preincubated with relevant phage mimotopes or mixtures thereof (Table page 16). In contrast, there was no inhibition of herceptin binding after preincubation by irrelevant control phages. Likewise, no reaction could be achieved when membranes of the Her-2/neu negative cell line HTB132 had been incubated with herceptin. A control antibody (Rituximab) directed against the antigen CD20, which is not expressed in SKBR3 membranes, could not produce any signal on these membranes either.

This test indicates that the tested phage mimotopes, in particular mixtures of CHPTLLWPDFC (SEQ ID NO: 9) and CYPSLLLHLPC (SEQ ID NO: 10), and of RSRL-WAVME (SEQ ID NO. 7), CLADPFIPHGC (SEQ ID NO: 8) and ATLMQIISQ (SEQ ID NO: 3), correctly render the natural epitope of the antibody herceptin on the Her-2/neu antigen.

TABLE 6

Inhibition of herceptin binding with phage mimotopes.

| # | | | | |
|---|---|---|---|---|
| 1 | SEQ ID NO: 9 | | | 30.2* |
| 2 | SEQ ID NO: 10 | | | 22.5 |
| 3 | SEQ ID NO: 11 | | | 26.2 |
| 4 | SEQ ID NO: 3 | | | 18.9 |
| 5 | SEQ ID NO: 9 | SEQ ID NO: 10 | | 38.5 |
| 6 | SEQ ID NO: 9 | SEQ ID NO: 11 | | 29.5 |
| 7 | SEQ ID NO: 9 | SEQ ID NO: 3 | | 30.2 |
| 8 | SEQ ID NO: 10 | SEQ ID NO: 11 | | 16.4 |
| 9 | SEQ ID NO: 10 | SEQ ID NO: 3 | | 14.9 |
| 10 | SEQ ID NO: 11 | SEQ ID NO: 3 | | 29.5 |
| 11 | SEQ ID NO: 9 | SEQ ID NO: 10 | SEQ ID NO: 11 | 25.8 |
| 12 | SEQ ID NO: 9 | SEQ ID NO: 11 | SEQ ID NO: 3 | 30.2 |
| 13 | SEQ ID NO: 10 | SEQ ID NO: 11 | SEQ ID NO: 3 | 17.1 |
| 14 | SEQ ID NO: 10 | SEQ ID NO: 10 | SEQ ID NO: 11  SEQ ID NO: 3 | 10.2 |
| 15 | Wild-type phage | | | 3 |

*Percent inhibition in comparison to uninhibited herceptin control in ELISA.

TABLE 7

Inhibition of herceptin binding with phage KLH-mimotopes.

| # | | | | | |
|---|---|---|---|---|---|
| 1 | SEQ ID NO: 6 | SEQ ID NO: 7 | SEQ ID NO: 8 | SEQ ID NO: 3 | 0* |
| 2 | SEQ ID NO: 6 | SEQ ID NO: 7 | SEQ ID NO: 8 | | 0 |
| 3 | SEQ ID NO: 6 | | SEQ ID NO: 8 | SEQ ID NO: 3 | 19.6 |
| 4 | | SEQ ID NO: 7 | SEQ ID NO: 8 | SEQ ID NO: 3 | 19.6 |
| 5 | SEQ ID NO: 6 | SEQ ID NO: 7 | | | 8.3 |
| 6 | SEQ ID NO: 6 | | SEQ ID NO: 8 | | 14.2 |
| 7 | SEQ ID NO: 6 | | | SEQ ID NO: 3 | 6.2 |
| 8 | | SEQ ID NO: 7 | SEQ ID NO: 8 | | 40.4 |
| 9 | | SEQ ID NO: 7 | | SEQ ID NO: 3 | 12.6 |
| 10 | | | SEQ ID NO: 8 | SEQ ID NO: 3 | 11.9 |
| 11 | SEQ ID NO: 6 | | | | 15.7 |
| 12 | SEQ ID NO: 7 | | | | 4.2 |
| 13 | SEQ ID NO: 8 | | | | 26.3 |
| 14 | SEQ ID NO: 3 | | | | 11.3 |
| 15 | KLH | | | | 0 |

*Percent inhibition in comparison to uninhibited herceptin control in ELISA

B) Specificity Testing of Rabbit Serums in ELISA.

For testing the rabbit serums for specific anti-Her-2/neu antibodies an ELISA was performed. As described above under point 3B), ELISA plates were coated with SKBR3 membranes, blocked and then in this case tested with serums of the immunized rabbits (preimmune serum versus immune serum) in a 1:10 dilution. Bound rabbit IgG was detected with a peroxidase labeled anti-rabbit IgG antibody and a color reaction again developed by substrate addition and read off.

TABLE 8

Immunization of rabbit with KLH-mimotope produces an IgG-specific titer increase against SKBR3 membranes.

| | Preimmune | Postimmune |
|---|---|---|
| SEQ ID NO: 7 | 0.31 | 0.57 |

This example shows that immunizations with mimotope KLH are suitable for inducing antibodies against the natural Her-2/neu on SKBR3 cells.

The invention claimed is:

1. A peptide mimotope comprising a peptide between about 9 and 14 amino acids comprising an amino acid sequence of SEQ ID NO: 3, SEQ ID NO: 6, SEQ ID NO: 7, SEQ ID NO: 8, SEQ ID NO: 9, SEQ ID NO: 10, or SEQ ID NO: 11.

2. The peptide mimotope of claim 1, wherein the peptide mimotope further contains a peptide linker.

3. The peptide mimotope of claim 1 further conjugated to a macromolecular carrier.

4. The peptide mimotope of claim 3, wherein multiple peptide mimotopes are conjugated to a macromolecular carrier.

5. The peptide mimotope of claim 3, wherein the peptide mimotope and the macromolecular carrier form a fusion protein.

6. The peptide mimotope of claim 3, wherein the macromolecular carrier is selected from the group consisting of: a tetanus toxoid, a keyhole limpet hemocyanin and an albumin carrier protein.

7. A composition comprising the peptide mimotope of claim 3 and an adjuvant.

8. A composition comprising the peptide mimotope of claim 4 and an adjuvant.

9. A composition comprising the peptide mimotope of claim 5 and an adjuvant.

10. A composition comprising the peptide mimotope of claim 6 and an adjuvant.

11. A method of inducing an immune response in a subject comprising administering the composition of claim 7 to said subject.

12. A method of inducing an immune response in a subject comprising administering the composition of claim 8 to said subject.

13. A method of inducing an immune response in a subject comprising administering the composition of claim 9 to said subject.

14. A method of inducing an immune response in a subject comprising administering the composition of claim 10 to said subject.

15. A method of producing a composition comprising: a) selecting a peptide mimotope of claim 1; and b) conjugating the peptide mimotope to a macromolecular carrier.

16. The method of claim 15, wherein the peptide mimotope further contains a peptide linker.

17. The method of claim 15, wherein the peptide mimotope and macromolecular carrier are a fusion protein.

18. The peptide minotope of claim 1, comprising an amino acid sequence of SEQ ID No: 3.

19. The peptide minotope of claim 1, comprising an amino acid sequence of SEQ ID No: 6.

20. The peptide minotope of claim 1, comprising an amino acid sequence of SEQ ID No: 7.

21. The peptide minotope of claim 1, comprising an amino acid sequence of SEQ ID No: 8.

22. The peptide minotope of claim 1, comprising an amino acid sequence of SEQ ID No: 9.

23. The peptide minotope of claim 1, comprising an amino acid sequence of SEQ ID No: 10.

24. The peptide minotope of claim 1, comprising an amino acid sequence of SEQ ID No: 11.

* * * * *